(12) United States Patent
Follmer et al.

(10) Patent No.: US 10,687,834 B2
(45) Date of Patent: Jun. 23, 2020

(54) ISCHEMIC STROKE DEVICE

(71) Applicant: DEPUY SYNTHES PRODUCTS, INC., Raynham, MA (US)

(72) Inventors: Brett Allen Follmer, Santa Clara, CA (US); Sheila Vallesteros Asuncion, Newark, CA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 218 days.

(21) Appl. No.: 15/983,719

(22) Filed: May 18, 2018

(65) Prior Publication Data

US 2019/0133628 A1     May 9, 2019

Related U.S. Application Data

(63) Continuation of application No. 13/801,979, filed on Mar. 13, 2013, now abandoned.

(51) Int. Cl.
| | |
|---|---|
| *A61B 17/22* | (2006.01) |
| *A61M 25/10* | (2013.01) |
| *A61B 17/221* | (2006.01) |

(52) U.S. Cl.
CPC ...... *A61B 17/22032* (2013.01); *A61B 17/221* (2013.01); *A61M 25/10* (2013.01); *A61B 2017/2212* (2013.01)

(58) Field of Classification Search
CPC ............ A61B 17/22032; A61B 17/221; A61B 2017/2212; A61M 25/10
See application file for complete search history.

(56) References Cited

U.S. PATENT DOCUMENTS

| | | | |
|---|---|---|---|
| 755,663 A | | 3/1904 | Hill |
| 4,425,908 A | * | 1/1984 | Simon ...................... A61F 2/01 128/899 |
| 4,643,184 A | * | 2/1987 | Mobin-Uddin ........... A61F 2/01 606/198 |
| 5,108,419 A | * | 4/1992 | Reger .............. A61B 17/32072 606/159 |
| 5,846,251 A | | 12/1998 | Hart |

(Continued)

FOREIGN PATENT DOCUMENTS

| | | |
|---|---|---|
| EP | 533511 A1 | 3/1993 |
| EP | 1452142 A1 | 9/2004 |

(Continued)

*Primary Examiner* — Phong Son H Dang

(57) ABSTRACT

An ischemic stroke device includes a telescoping member, a first or proximal expandable member connected to the telescoping support member, and a second or distal expandable member connected to the first expandable member. A proximal portion of the first expandable member is attached to a distal end of an outer shaft of the telescoping support member, and a distal end of the first expandable member is attached to a distal portion of an inner core wire of the telescoping support member. The proximal end of the second expandable member is permanently joined to the distal end of the inner core wire. The first expandable member everts to cover the second expandable member that is used to capture an obstruction or clot, prior to pulling the obstruction or clot into a catheter for removal from a patient's vasculature.

20 Claims, 2 Drawing Sheets

(56) References Cited

U.S. PATENT DOCUMENTS

| | | | |
|---|---|---|---|
| 5,855,565 A * | 1/1999 | Bar-Cohen | A61M 29/02 604/104 |
| 6,210,370 B1 | 4/2001 | Chi-Sing | |
| 6,635,068 B1 | 10/2003 | Dubrul | |
| 7,220,271 B2 | 5/2007 | Clubb | |
| 7,331,980 B2 | 2/2008 | Dubrul | |
| 7,556,635 B2 * | 7/2009 | Mazzocchi | A61B 17/12022 606/108 |
| 7,604,650 B2 | 10/2009 | Bergheim | |
| 7,875,050 B2 * | 1/2011 | Samson | A61B 17/221 606/200 |
| 8,052,640 B2 * | 11/2011 | Fiorella | A61B 17/22 604/103.08 |
| 8,070,791 B2 | 12/2011 | Ferrera | |
| 8,137,376 B2 | 3/2012 | Clubb | |
| 8,252,017 B2 | 8/2012 | Paul, Jr. | |
| 8,317,748 B2 | 11/2012 | Fiorella | |
| 2002/0138095 A1 * | 9/2002 | Mazzocchi | A61B 17/12022 606/200 |
| 2006/0259067 A1 * | 11/2006 | Welch | A61F 2/01 606/200 |
| 2007/0208370 A1 * | 9/2007 | Hauser | A61F 2/01 606/200 |
| 2008/0071307 A1 | 3/2008 | DeBruyne | |
| 2008/0262528 A1 | 10/2008 | Martin | |
| 2008/0262532 A1 | 10/2008 | Martin | |
| 2009/0299393 A1 | 12/2009 | Martin | |
| 2010/0168785 A1 | 7/2010 | Parker | |
| 2011/0060359 A1 | 3/2011 | Hannes | |
| 2011/0152920 A1 | 6/2011 | Eckhouse | |
| 2011/0288572 A1 * | 11/2011 | Martin | A61B 17/221 606/159 |
| 2012/0041459 A1 | 2/2012 | Fiorella | |
| 2012/0197285 A1 * | 8/2012 | Martin | A61B 17/221 606/200 |
| 2013/0317589 A1 * | 11/2013 | Martin | A61B 17/3207 623/1.2 |

FOREIGN PATENT DOCUMENTS

| | | |
|---|---|---|
| JP | 2011508635 A | 3/2011 |
| WO | WO 1999016362 A1 | 4/1999 |
| WO | WO 2004093966 A1 | 11/2004 |
| WO | WO 2009055782 A1 | 4/2009 |
| WO | WO 2012162437 A1 | 11/2012 |

* cited by examiner

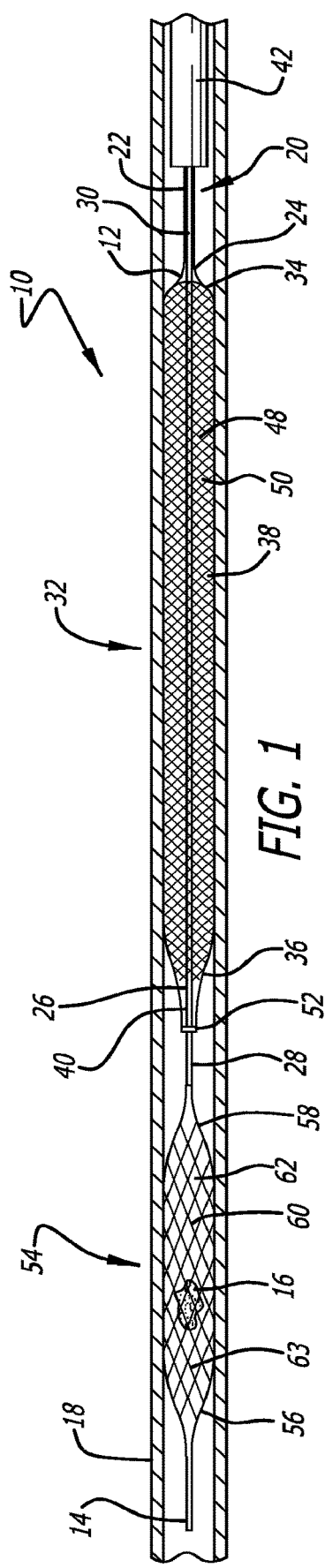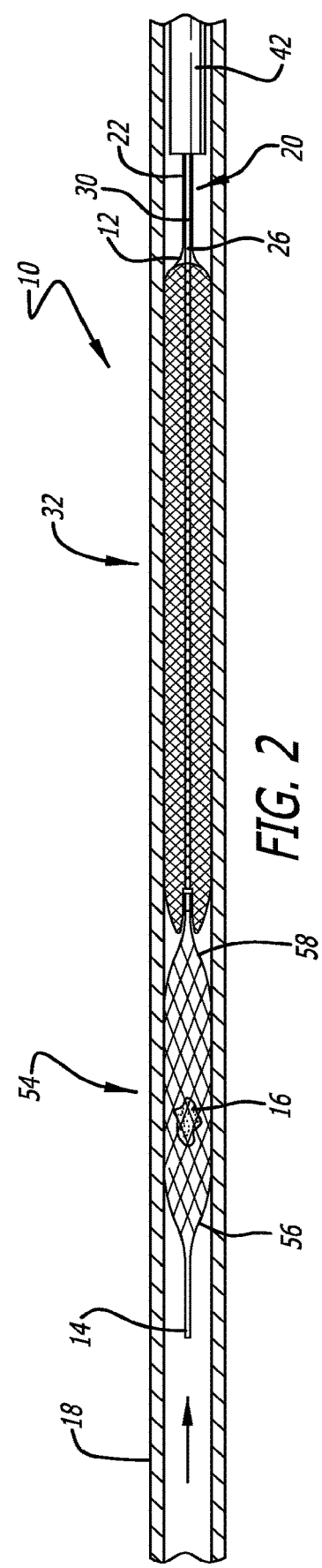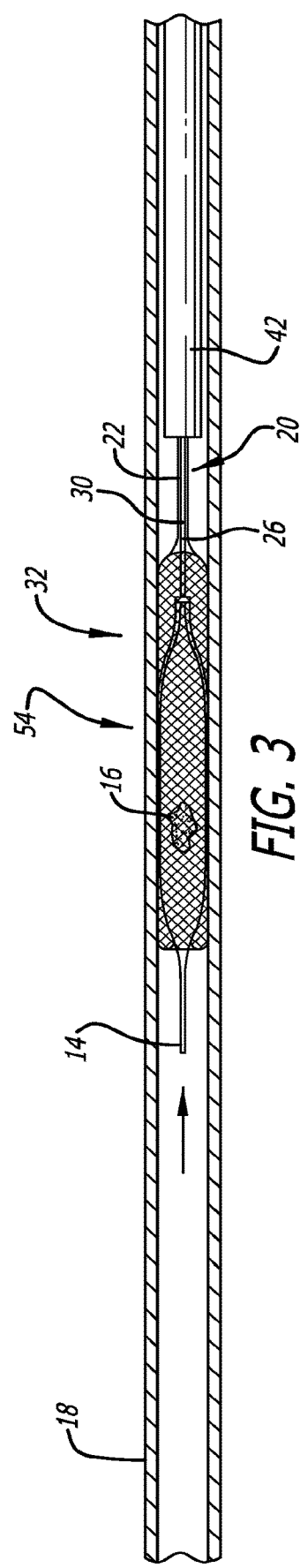

ISCHEMIC STROKE DEVICE

CROSS REFERENCE TO RELATED PCT APPLICATION

This application is a continuation of U.S. patent application Ser. No. 13/801,979, filed Mar. 13, 2013.

BACKGROUND OF THE INVENTION

The present invention relates to an apparatus and method for increasing blood flow through an obstructed blood vessel and, more particularly relates to an apparatus and method for removal of at least a portion of an obstruction such as a clot from an obstructed blood vessel for treatment of ischemic stroke.

A common treatment for ischemic stroke is the use of a thrombectomy device to physically remove an obstruction such as a blood clot from the affected artery. One such thrombectomy device typically is advanced through a microcatheter into the vasculature, and is deployed into an obstruction or clot in the vasculature by pulling back on the microcatheter, allowing the thrombectomy device to capture at least a portion of the obstruction or clot, and the thrombectomy device is then retrieved by withdrawing the thrombectomy device into a catheter such as a guide catheter or an intermediate catheter. To prevent the loss of the captured portion of the obstruction or clot when the thrombectomy device is being retrieved, a balloon guide catheter or aspiration catheter may be used. Aspiration is performed by attaching a syringe to a proximal end of the guide catheter and pulling a vacuum in the syringe, while simultaneously pulling the retrieving the thrombectomy device and the captured portion of the obstruction or clot into the guide catheter. A balloon guide may be inflated just prior to retrieval of the thrombectomy device and the captured portion of the obstruction or clot in order to arrest blood flow. The thrombectomy device with the captured portion of the obstruction or clot is then pulled back into the balloon guide catheter.

One embolic protection device is known that includes inner and outer tubular members and a flexible everting filter portion that is attached at one end to a distal end of the inner tubular member, and that is attached at a second end to a distal end of the outer tubular member, so that the inner and outer tubular members are movable relative to one another to position the filter portion within the body vessel. The filter portion is movable from a collapsed, everted configuration to an expanded, generally non-everted deployed configuration. The filter portion expands radially outward to engage the filter body with an enclosing vessel wall, and also allows the passage of blood cells, while preventing the passage of captured emboli or thrombi through the filter portion.

Another similar invertible filter is known that includes a guiding member configured to slidably engage a tubular filter portion that extends distally from the guiding member and is configured to evert to form a concave shape for capturing emboli, while allowing blood cells to pass through the filter portion.

Another type of device for treating a vascular condition is known that includes a graft, and first and second support members such as stents attached to distal and proximal regions of the graft. The first and second stents are deployed distally and proximally of a vascular condition, and the graft can be everted to form a pocket to trap emboli during treatment of the vascular condition.

Another device is known that includes a capturing section configured that can be inverted within a translating section by proximal movement of a leading wire when an open proximal end of the translating section engages resistance, and the size of the capturing section is reduced to enable the capturing section to re-enter a catheter.

Another device for increasing blood flow through an obstructed blood vessel is known that includes an expandable member that is positioned within a blood vessel and radially adjacent to at least a portion of an obstruction, and that is expanded to bring at least a portion of the expandable member into contact with the obstruction. The expandable member is made of a mesh having a plurality of interstices that allow one or more fragments of the obstruction to pass into and be retained within the expandable member when an outward radial force is exerted on the obstruction by the expandable member.

However, whenever a captured obstruction or clot is retrieved into any type of catheter there is always a risk of some or all of the obstruction or clot being released into a patient's vasculature. In many cases some or all of the obstruction or clot is captured on the outside of the thrombectomy device. As the thrombectomy device is pulled back into a catheter, some or all of the obstruction or clot may be scraped off, sending one or more pieces of the obstruction or clot downstream to another artery, after which one or more dislodged pieces of the obstruction or clot will then need to be removed, adding to the length of time and complexity of the procedure. Smaller pieces of the clot also may go further downstream to smaller vessels that are not accessible with current thrombectomy devices.

It would be desirable to provide an apparatus and method for removal of at least a portion of an obstruction or clot from an obstructed blood vessel for treatment of ischemic stroke that provides a cover over the secured obstruction or clot prior to drawing the secured obstruction or clot into a catheter, in order to reduce the risk of the obstruction or clot being scraped off or otherwise losing one or more pieces of the obstruction or clot being retrieved during a thrombectomy procedure. The present invention meets these and other needs.

SUMMARY OF THE INVENTION

Briefly and in general terms, the present invention provides for an apparatus and method for removal of at least a portion of an obstruction such as a clot from an obstructed blood vessel for treatment of a condition of a patient's vasculature such as ischemic stroke. The apparatus and method of the invention helps to reduce the risk of losing one or more pieces of an obstruction such as a clot during a thrombectomy procedure by providing a first or proximal expandable member that functions as a cover element that can evert to enfold and enclose a second or distal expandable member used to secure the obstruction or clot prior to pulling the secured obstruction or clot into a catheter for removal from the patient's vasculature. The first or proximal expandable member covers over not only the captured obstruction or clot, but also portions of the obstruction or clot which may be only partially captured, such as a portion of the obstruction stuck to or extending from the outside of the second or distal expandable member, to help to prevent the clot from being scraped off when the clot is pulled into a catheter. The close proximity of the first and second expandable members also allows the captured obstruction or clot to be covered almost immediately, which also can help to reduce the possibility of fragmentation of the obstruction or clot. A telescoping support member connected to the first or proximal expandable member also allows a user to initiate the process of causing the first or proximal expandable member to evert to enfold and enclose the second or distal expandable member used to secure the obstruction or clot.

The present invention accordingly provides for an apparatus and method for removal of at least a portion of an obstruction from an obstructed blood vessel for treatment of ischemic stroke. The apparatus includes a telescoping support member, a first or proximal expandable member connected to the telescoping support member, and a second or distal expandable member connected to the first or proximal expandable member. The telescoping support member includes an outer tubular shaft and an inner elongate member that extends through and is slidable within the outer tubular shaft. The first or proximal expandable member has a proximal end that is attached to a distal end of the outer tubular shaft of the telescoping support member, and a distal end of the first or proximal expandable member is attached to a distal portion of the inner elongate member. The first or proximal expandable member preferably has a radially compressed configuration and a radially expanded configuration, as well as a longitudinally extended configuration with proximal and distal ends of the first or proximal expandable member disposed at opposing ends of the first or proximal expandable member, and an everted configuration with the distal end of the first or proximal expandable member withdrawn within the tubular body of the first or proximal expandable member and adjacent to the proximal end of the first or proximal expandable member. The second or distal expandable member preferably has a closed distal end and a closed proximal end, and a tubular mesh body extending between the proximal and distal ends of the second or distal expandable member, and is configured to be deployed into an obstruction within the blood vessel. The closed proximal end of the second or distal expandable member preferably also is permanently joined to the distal end of the inner elongate member of the telescoping support member. The second or distal expandable member also preferably has a radially compressed configuration and a radially expanded configuration, and the tubular mesh body of the second or distal expandable member preferably is configured to radially expand into contact with at least a portion of the obstruction or clot such that a portion of the obstruction or clot is dislodged to enhance blood flow through the blood vessel. In a presently preferred aspect, the tubular mesh body includes a plurality of interstices, at least a portion of which are adapted to allow passage of at least one dislodged portion of the obstruction therethrough in a radial direction into the tubular mesh body.

In another presently preferred aspect, the tubular body of the first or proximal expandable member includes a plurality strands defining a plurality of interstices therebetween. In another presently preferred aspect, the tubular body of the first or proximal expandable member includes a radiopaque band permanently attached to the distal end of the first or proximal expandable member. In another presently preferred aspect, the tubular mesh body of the second or distal expandable member comprises a plurality of strands, and the plurality of strands may form first and second meshes. In another presently preferred aspect, each of the plurality of strands is oriented in at least one of a helical, longitudinal, and radial direction with respect to the tubular mesh body.

In another presently preferred aspect, the second or distal expandable member is at least partially constructed of a self-expanding material, and the second or distal expandable member is configured to dislodge the obstruction by fracturing a portion of the obstruction or by extruding a portion of the obstruction.

In another presently preferred aspect, the second or distal expandable member includes at least one radiopaque portion. In another presently preferred aspect, the second or distal expandable member is at least partially adapted to elute a pharmaceutical agent. In another presently preferred aspect, the pharmaceutical agent is adapted to at least partially lyse the at least one fragment. In another presently preferred aspect, the tubular mesh body of the second or distal expandable member includes a distal portion and a proximal portion, the distal portion of the tubular mesh body being formed of a first mesh, and the proximal portion of the tubular mesh body being made of a second mesh having a plurality of second interstices, at least one of the second interstices being adapted to selectively allow passage of at least one fragment therethrough. In another presently preferred aspect, the first mesh is formed integrally with the second mesh. In another presently preferred aspect, at least one of the first interstices is defined by a plurality of first strands, and at least one of the plurality of first strands is adapted to penetrate into the obstruction to longitudinally separate the at least one fragment from a remaining portion of the obstruction. In another presently preferred aspect, at least one of the second interstices is defined by a plurality of second strands, at least one of the plurality of second strands is adapted to break the at least one fragment into a plurality of subfragments, and at least one of the second interstices is adapted to selectively allow passage therethrough of at least one subfragment to release the at least one subfragment from the second or distal expandable member. In another presently preferred aspect, at least one of the plurality of second interstices is smaller than at least one of the plurality of first interstices. In another presently preferred aspect, a size of at least one of the plurality of second interstices is chosen on the basis of an allowable particulate size of the blood vessel. In another presently preferred aspect, the tubular mesh body of the second or distal expandable member is configured to compress at least a portion of the obstruction against a vessel wall of the blood vessel.

In the method of the invention, movement of the inner elongate member in a proximal direction relative to the outer tubular shaft of the telescoping support member moves the first or proximal expandable member between the longitudinally extended configuration and the everted configuration such that the first or proximal expandable member covers, enfolds or envelopes the second or distal expandable member.

Other features and advantages of the present invention will become more apparent from the following detailed description of the preferred embodiments in conjunction with the accompanying drawings, which illustrate, by way of example, the operation of the invention.

BRIEF DESCRIPTION OF THE DRAWINGS

FIG. 1 is an elevational, schematic diagram of the apparatus of the invention disposed within a patient's vasculature, showing the first and second expandable members in radially expanded configurations within the vasculature, with an obstruction or clot captured within the second or distal expandable member, according to the invention.

FIG. 2 is an elevational, schematic diagram similar to FIG. 1, showing the first or proximal expandable member beginning to evert to enfold and cover the second or distal expandable member as the second or distal expandable member is drawn into the first or proximal expandable member.

FIG. 3 is an elevational, schematic diagram similar to FIG. 2, showing the first or proximal expandable member everted to enfold and cover the second or distal expandable member, which has been drawn into the first or proximal expandable member.

DETAILED DESCRIPTION OF THE PREFERRED EMBODIMENTS

Figure 4:
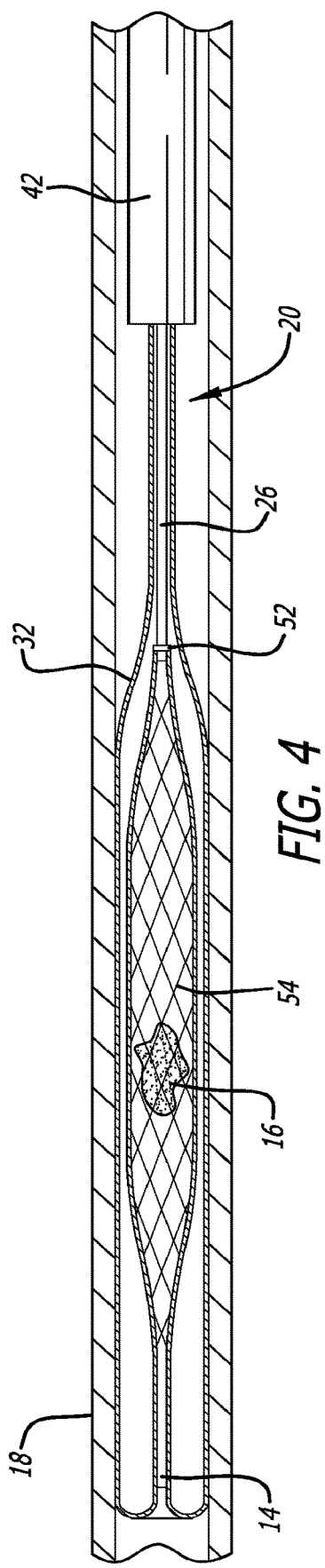
FIG. 4 is an enlarged cross-sectional view similar to FIG. 3.

Referring to the drawings, which are provided by way of example, and not by way of limitation, the present invention provides for an apparatus 10 having a proximal end 12 and a distal end 14, for removal of at least a portion of an obstruction 16, such as a clot, for example, from an obstructed blood vessel in a patient's vasculature 18, such as for treatment of ischemic stroke, for example.

The apparatus includes a telescoping support member 20, including an outer tubular shaft 22 having a distal end 24, and an inner elongate member or core advancement wire 26 having a distal end 28 and a proximal portion 30, and extending through the outer tubular shaft and slidable within the outer tubular shaft. The apparatus also includes a first, proximal expandable member or cover element 32 having a proximal end 34 and a distal end 36, and a tubular body 38 extending between the proximal and distal ends of the first or proximal expandable member. The proximal end of the first or proximal expandable member is preferably permanently attached to the distal end of the outer tubular shaft of the telescoping support member, and the distal end of the first or proximal expandable member is preferably permanently attached to a distal portion 40 of the inner elongate member or core advancement wire. The first or proximal expandable member has a radially expanded configuration configured to engage the inner surface of a blood vessel in the patient's vasculature, as shown in FIGS. 1-4, and a radially compressed configuration, such as when the first or proximal expandable member is disposed within and constrained by an introducer or delivery catheter 42 having an inner lumen (not shown). The first or proximal expandable member preferably is dimensioned to fit within the inner lumen of the catheter in the radially compressed configuration, and is configured to be constrained from expanding when the first or proximal expandable member is contained within the catheter.

Referring to FIG. 1, in the radially expanded configuration, the first or proximal expandable member preferably also has a longitudinally extended configuration with the proximal and distal ends of the first or proximal expandable member disposed at opposing ends of the first or proximal expandable member, and an everted configuration, best shown fully in FIG. 4, with the distal end of the first or proximal expandable member withdrawn within the tubular body of the first or proximal expandable member adjacent to the proximal end of the first or proximal expandable member. The tubular body of the first or proximal expandable member preferably includes a plurality strands of material 48 forming a proximal braided portion of the apparatus, defining a plurality of interstices 50 therebetween. The first or proximal expandable member also preferably includes at least one radiopaque portion, such as a radiopaque band 52 that is permanently attached to the distal end of the first or proximal expandable member.

The apparatus also includes a second, distal expandable member 54 at the distal end of the apparatus, that is configured to be deployed into an obstruction or clot within the blood vessel in the patient's vasculature. The second or distal expandable member preferably includes a closed distal end 56 a closed proximal end 58, and a tubular mesh body 60 extending between the proximal and distal ends of the second or distal expandable member. The closed proximal end of the second or distal expandable member preferably is permanently joined to the distal end of the inner elongate member of the telescoping support member, such as by soldering, for example, although the second or distal expandable member may alternatively be permanently joined to the distal end of the inner elongate member of the telescoping support member by other similar suitable means, such as by adhesive or by heat shrinkable tubing, or combinations thereof, for example.

The tubular mesh body of the second, distal expandable member preferably is configured to radially expand into contact with at least a portion of the obstruction or clot in the blood vessel, such that a portion of the obstruction is dislodged to enhance blood flow through the blood vessel. The tubular mesh body preferably includes a plurality of interstices 62, and at least a portion of the interstices preferably are configured to allow passage of at least one dislodged portion of the obstruction therethrough in a radial direction into the tubular mesh body. The tubular mesh body can be formed to include a plurality of strands 63 forming first and second meshes, wherein each of the strands may be oriented in at least one of a helical, longitudinal, and radial direction with respect to the tubular mesh body. In a presently preferred aspect, the second or distal expandable member is configured to dislodge the obstruction or clot by fracturing a portion of the obstruction, by extruding a portion of the obstruction, or a combination thereof. In another presently preferred aspect, the second or distal expandable member is at least partially constructed of a superelastic and/or self-expanding material, such as a nickel-titanium alloy which has been memory-shaped into an expanded condition and is compressed into a collapsed condition before use. The second or distal expandable member is constrained in the compressed condition by the introducer or delivery catheter, and preferably self-expands into the expanded condition upon removal from the introducer or delivery catheter. The second or distal expandable member may also include one or more radiopaque portions, such as one or more additional radiopaque bands, for example. In another presently preferred aspect, the second or distal expandable member is at least partially adapted to elute a pharmaceutical agent, such as a pharmaceutical agent designed to at least partially lyse the obstruction or fragment of the obstruction.

Figure 5:
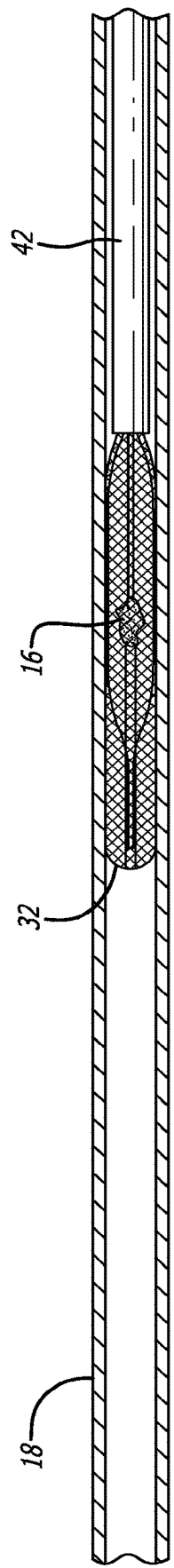
FIG. 5 is an elevational, schematic diagram similar to FIG. 3, showing the first and second expandable members with the captured obstruction or clot being retrieved and withdrawn into a catheter.

The tubular mesh body may include a first mesh in a distal portion of the tubular mesh body having a plurality of first interstices, and a second mesh in a proximal portion of the tubular mesh body being made of having a plurality of second interstices, with at least one of the second interstices being configured to selectively allow passage of at least one fragment therethrough. The first mesh can be formed integrally with the second mesh, for example. At least one of the first interstices may be defined by a plurality of first strands, in which case at least one of the plurality of first strands may be adapted to penetrate into the obstruction to longitudinally separate the at least one fragment from a remaining portion of the obstruction. At least one of the second interstices may be defined by a plurality of second strands, in which case at least one of the plurality of second strands may be adapted to break one or more fragments of the obstruction or clot into a plurality of subfragments, and at least one of the second interstices may be adapted to selectively allow passage of at least one subfragment therethrough to be released from the second or distal expandable member. In another presently preferred aspect, one or more of the plurality of second interstices can be smaller than one or more of the plurality of first interstices, and the size of one or more of the plurality of second interstices may be chosen on the basis of an allowable particulate size of the blood vessel. The tubular mesh body may also be configured to compress at least a portion of the obstruction against a vessel wall of the blood vessel Referring to FIGS. 2 and 3, in the method of operation of the device of the invention, when the distal element is pulled back, the proximal braided portion starts to evert, initiating covering the distal element, much like pulling a sock over a foot, so that movement of the inner elongate member in a proximal direction relative to the outer tubular shaft of the telescoping support member moves the first or proximal expandable member between the longitudinally extended configuration and the everted configuration, so that the first or proximal expandable member covers, envelopes or enfolds the second or distal expandable member as shown in FIG. 4, as well as any of the obstruction that may be only partially captured in the second or distal expandable member, such as a portion of the obstruction stuck to or extending from the outside of the second or distal expandable member, for example, so that the second or distal expandable member and captured obstruction material can be withdrawn and retrieved into a catheter, as is illustrated in FIG. 5.

It will be apparent from the foregoing that while particular forms of the invention have been illustrated and described, various modifications can be made without departing from the spirit and scope of the invention. Accordingly, it is not intended that the invention be limited, except as by the appended claims.

The invention claimed is:

1. A method of removing of at least a portion of an obstruction from an obstructed blood vessel for treatment of ischemic stroke, comprising the steps of:
providing a telescoping support member including an outer tubular shaft and an inner elongate member extending through said outer tubular shaft and slidable within said outer tubular shaft, said outer tubular shaft having a distal end, and said inner elongate member having a distal end and a proximal end;
providing a first expandable member having a proximal end and a distal end and a tubular body extending between the proximal and distal ends of the first expandable member, said proximal end of said first expandable member being attached to said distal end of said outer tubular shaft of said telescoping support member, and said distal end of said first expandable member being attached to a distal portion of said inner elongate member, said first expandable member having a radially compressed configuration and a radially expanded configuration, and said first expandable member having a longitudinally extended configuration with said proximal and distal ends of said first expandable member disposed at opposing ends of said first expandable member, and an everted configuration with said distal end of said first expandable member withdrawn within said tubular body of said first expandable member adjacent to said proximal end of said first expandable member; and
providing a second expandable member configured to be deployed into an obstruction within the blood vessel, and a tubular mesh body extending between the proximal and distal ends of the second expandable member, said proximal end of said second expandable member being permanently joined to said distal end of said inner elongate member of said telescoping support member,
radially expanding said tubular mesh body into contact with at least a portion of the obstruction such that a portion of the obstruction is dislodged to enhance blood flow through the blood vessel, said tubular mesh body including a plurality of interstices, at least a portion of the interstices being adapted to allow passage of at least one dislodged portion of the obstruction therethrough in a radial direction into the tubular mesh body,
moving said inner elongate member in a proximal direction relative to said outer tubular shaft of the telescoping support member such that the first expandable member moves between said longitudinally extended configuration and said everted configuration such that said first expandable member envelopes said second expandable member and said second expandable member is disposed radially within said first expandable member.

2. The method of claim 1, wherein said tubular body of said first expandable member comprises a plurality strands defining a plurality of interstices therebetween.

3. The method of claim 1, wherein said tubular body of said first expandable member comprises a radiopaque band permanently attached to said distal end of said first expandable member.

4. The method of claim 1, wherein said tubular mesh body of said second expandable member comprises a plurality of strands.

5. The method of claim 4, wherein said plurality of strands form first and second meshes.

6. The method of claim 4, wherein each of said plurality of strands is oriented in at least one of a helical, longitudinal, and radial direction with respect to the tubular mesh body.

7. The method of claim 1, wherein said second expandable member dislodges the obstruction by fracturing a portion of the obstruction.

8. The method of claim 1, wherein said second expandable member dislodges the obstruction by extruding a portion of the obstruction.

9. The method of claim 1, wherein said second expandable member is at least partially constructed of a self-expanding material.

10. The method of claim 1, wherein said obstruction comprises a clot.

11. The method of claim 1, wherein said second expandable member includes at least one radiopaque portion.

12. The method of claim 1, wherein said second expandable member elutes a pharmaceutical agent.

13. The method of claim 12, wherein said pharmaceutical agent is adapted to at least partially lyse an at least one fragment.

14. The method of claim 1, wherein said tubular mesh body of said second expandable member includes a distal portion and a proximal portion, the distal portion of the tubular mesh body being formed of a first mesh, and the proximal portion of the tubular mesh body being made of a second mesh having a plurality of second interstices, at least one of the second interstices being adapted to selectively allow passage of at least one fragment therethrough.

15. The method of claim 14, wherein said first mesh is formed integrally with the second mesh.

16. The method of claim 14, wherein at least one of a first interstices is defined by a plurality of first strands, and at least one of the plurality of first strands is adapted to penetrate into the obstruction to longitudinally separate the at least one fragment from a remaining portion of the obstruction.

17. The method of claim 14, wherein at least one of the second interstices is defined by a plurality of second strands, at least one of the plurality of second strands is adapted to break the at least one fragment into a plurality of subfragments, and at least one of the second interstices is adapted to selectively allow passage therethrough of at least one subfragment to release the at least one subfragment from the second expandable member.

18. The method of claim 14, wherein a size of at least one of the plurality of second interstices is chosen on the basis of an allowable particulate size of the blood vessel.

19. The method of claim 14, wherein said tubular mesh body of said second expandable member compresses at least a portion of the obstruction against a vessel wall of the blood vessel.

20. The method of claim 1, wherein the proximal and distal ends of the second expandable member are closed ends.

* * * * *